United States Patent [19]
Kimmel

[11] Patent Number: 5,101,822
[45] Date of Patent: Apr. 7, 1992

[54] TRACHESOSTOMY TUBE STABILIZER

[76] Inventor: Erika E. Kimmel, 7361 S. W. 16th St., Miami, Fla. 33155

[21] Appl. No.: 502,779

[22] Filed: Apr. 2, 1990

[51] Int. Cl.⁵ .............................................. A61M 16/00
[52] U.S. Cl. ............................ 128/207.14; 128/207.17
[58] Field of Search ...................... 128/200.26, 207.14, 128/207.15, 207.17, DIG. 15, DIG. 26

[56] References Cited

U.S. PATENT DOCUMENTS

| | | | |
|---|---|---|---|
| 2,669,231 | 2/1954 | Fisher | 128/DIG. 26 |
| 2,765,792 | 10/1956 | Nichols | 128/207.17 |
| 3,987,798 | 10/1976 | McGinnis | 128/DIG. 26 |
| 4,054,952 | 10/1977 | Swallow | 128/DIG. 15 |
| 4,081,150 | 3/1978 | Tyson | 128/DIG. 15 |
| 4,088,136 | 5/1978 | Hasslinger et al. | 128/DIG. 26 |
| 4,313,437 | 2/1982 | Martin | 128/207.17 |
| 4,331,144 | 5/1982 | Wapner | 128/207.17 |
| 4,367,735 | 1/1983 | Dali | 128/207.17 |
| 4,489,723 | 12/1984 | Simons et al. | 128/207.17 |
| 4,569,348 | 2/1986 | Hasslinger | 128/DIG. 15 |
| 4,592,351 | 6/1986 | Smith et al. | 128/207.17 |

*Primary Examiner*—Edgar S. Burr
*Assistant Examiner*—Aaron J. Lewis
*Attorney, Agent, or Firm*—Robert M. Schwartz; Edward I. Mates

[57] ABSTRACT

A device for supporting and maintaining a tracheostomy tube in a midline position relative to the stoma of a tracheostomy includes a neck plate support piece that corresponds to the neck plate of a tracheostomy tube to provide support directly over the stoma of the tracheostomy helping to secure the tracheostomy tube. Tracheostomy tapes extend from a front collar piece in opposite directions from the neck plate support piece around and behind the neck of a patient and are threaded through a plurality of longitudinally aligned loops that help maintain the tapes positioned centrally on the collar. Mating male and female snaps on the front and rear collar pieces remain attached even after conventional tapes and Velcro fastenings are loosened.

The device also contains a porous polytetrafluoroethylene (PTFE) material covering instead of Velcro exposed directly to the stoma. The PTFE is easy to maintain even in the presence of contaminating secretions from the stoma of the tracheostomy and reduces the need for frequent replacement of the device.

10 Claims, 7 Drawing Sheets

TRACHESOSTOMY TUBE STABILIZER

FIELD OF THE INVENTION

This invention relates to a support for tracheostomy tubes and other like medical appliances, particularly those pivotally supported relative to a swivel plate having flanges provided with flange holes.

BACKGROUND OF THE INVENTION

Traditionally, tracheostomy tubes were customarily supported in place by a thin cotton tape extending around the neck of a patient, and the ends of the tape were tied to openings in the flanges of a flanged neck plate of the tracheostomy tube in a variety of ways. One method of securing the cotton tape to two openings in the flanges of the neck plate is to cut a small opening lengthwise in the cotton tape in one end, then thread the other end of the cotton tape through one of the two openings in the flange of the neck plate and bring it through the opening cut in the cotton tape on the other end and pull it through, thereby securing one end of the cotton tape to the opening in the flange of the neck plate. The free end of the cotton tape is then brought behind and around the neck of a patient and threaded through the opening in the flange of the neck plate on the opposite side. The cotton tape is then pulled back and tied in a knot to itself to secure the tracheostomy tube to the patient.

Other methods of securing the tracheostomy tube to a patient using the cotton tape include using the same method as described above to attach the cotton tapes to the openings in the flanges of the neck plate after having first cut the cotton tape in two pieces, of different lengths, then bringing the longer piece of the cotton tape behind and around the neck of a patient and tying it in a knot to the other end of the shorter cotton tape on the opposite side of the neck.

Knots may be tied directly to openings in the flanges of the neck plate with the longer piece of cotton tape again being secured to the shorter end in the manner previously described.

The cotton tape may be threaded through the openings in the flanges of the neck plate as one piece with the ends of the tapes being knotted together to one side of the neck of a patient with an intermediate length of the tape extending horizontally directly over or under the tracheostomy tube which is centered in the neck plate, or the knot may be tied with the two free ends of the cotton tape brought up from below the openings in the flanges of the neck plate and threaded through with the ends tied in a knot either directly above or below the tracheostomy tube.

The cotton tape, which is very light and flimsy, has a tendency to curl and roll, forming a rope-like strap. This can be uncomfortable to a patient and may cause irritation to the skin from chafing.

The methods of securing the cotton tape to the openings in the flanges of the neck plate of a tracheostomy tube device to the neck of a patient may cause injury to the soft tissues surrounding the tracheostomy. This injury factory is the result of the tracheostomy tube device deviating from the midline of the trachea within the neck of a patient toward the side of the neck where the ends of the cotton tape are tied together. Pressure is exerted on the soft tissues until the tape is readjusted to

2 displace the tracheostomy tube device from engaging the stoma wall.

When the cotton tape ends are tied in a knot directly over or beneath the tracheostomy tube which is centered in the neck plate of the tracheostomy tube device, pressure is exerted directly over the stoma of the tracheostomy.

These traditional methods of securing the cotton tape to the tracheostomy tube device to the neck of a patient contribute to the potential for injury of the soft tissues surrounding the stoma of a tracheostomy.

When the tracheostomy tube device is not maintained in the midline position within the trachea of the neck of a patient, the soft tissues surrounding the original incision forming the tracheostomy may erode from the constant pressure being exerted on the walls of the stoma, thus enlarging the opening of the stoma.

Infection and the loss of a good air seal may result in a patient with a damaged tracheostomy stoma. Considerable pain and discomfort may be experienced by a patient with a damaged tracheostomy stoma.

Cotton tapes may be secured too tightly around the neck of a patient, causing pain and a discomfort as well as possibly impeding the return of blood flow from the head and neck of a patient.

Cotton tapes may be secured too loosely, the knots may loosen or become untied causing the inadvertent loss of the airway or displacement of the tracheostomy tube device into the subcutaneous tissues of a patient's neck and/or chest areas causing further complications to a patient.

U.S. Pat. No. 4,569,248 to Hasslinger, issued Feb. 11, 1986, reports that the separable fasteners such as those described in U.S. Pat. Nos. 2,7171,437 and 3,009,235 which are marketed under the registered trademark VELCRO brand hook and loop fasteners by Velcro USA, Inc., 521 Fifth Avenue, New York, N.Y. have gained wide acceptance because of the properties of the mating hooks and loops. A surface defined by the hooks exposed on an outer surface of one flexible tape is merely placed into face-to-face relationship with a surface defined by the loops exposed on an outer surface of an overlapping tape so that a large number of hooks engage a large number of loops and therefore are able to resist separation of the tapes by forces parallel to the interfacial plane of engagement but are readily separable by peeling forces applied substantially normal to this interfacial plane. These fastening devices are generally formed of a sheet of synthetic woven or knitted fabric having raised threads of synthetic material, such as nylon, which are napped or unnapped to provide a pile surface defined by a plurality of loops, and which may be thermally treated to become semi-rigid. Certain of the loops may then be cut along one side near their outer extremity to form hooks.

These fasteners have been used in numerous applications, particularly because of their unique touch and close fastener capability as well as their fastening strength. The unique fastening capability of these hook and loop type engaging elements have been applied to particular use to create various fastener arrangements.

In particular, fasteners of this type are used either along or as major components of strapping devices of various types. The applications of these separable hook and loop type fasteners have reduced the need for traditional strap fastening devices such as buckles. Also, to the extent that earlier fastening devices did not generally facilitate variable and precise fastening, these separable fasteners have provided substantial advantages.

The advent of VELCRO fastening means made it possible to adjust the length of the VELCRO fastening means to conform more closely to the length of the circumference of the neck about which the VELCRO fastening means is fastened. However, VELCRO fastening means are not as permanent.

These VELCRO fastening means have the characteristics of being designed in a straight line with the VELCRO fastening means in the form of tapes extending from the back of these one or two piece bands. When these VELCRO tapes are applied to the neck of a patient, the VELCRO tracheostomy tapes that are threaded through the openings in the flanges of the neck plate tend to rest against the top of the openings in the flanges of the neck plate causing a firm, upward pressure on the stoma of the tracheostomy.

The materials used in the manufacture of the various types of VELCRO fastening means tend to stretch and lose their basic shape and strength with repeated use and washings The fabric used in these VELCRO fastening means may weaken, with the tracheostomy tapes of these VELCRO fastening means potentially loosening and slipping out of the openings in the flanges of the neck plate. The loss of a patient's airway may result with the failure of the VELCRO fastening means to remain securely fastened. The elastic band of the VELCRO fastening means loses its elasticity with repeated use.

The addition of ventilator tubing and indwelling suction equipment on a patient who requires mechanical assistance with breathing and removal of pulmonary secretions causes additional stress to be placed on the VELCRO fastening means for securing and maintaining a tracheostomy tube properly within the neck of a patient.

In addition, prior art devices that include the traditional cotton tape and the Velcro-type bands for supporting a tracheostomy tube are exposed to mucous, blood, sweat, wound drainage from the tracheostomy stoma or from draining surgical wounds on the head or neck of a patient. Exposure of the cotton tapes or bands of VELCRO fastening means to the aforementioned contaminants requires that the cotton tape be changed, or the VELCRO fastening means removed and washed, replaced in the meantime with a fresh VELCRO fastening means. Failure to change soiled tracheostomy tapes of the cotton tape type or the VELCRO fastening means may result in skin irritation and/or wound infection in a patient who has prolonged exposure to the previously described secretions.

DISCUSSION OF RELEVANT ART

Several patents have been issued with the objectives of providing a band which is comfortable to the patient, provides for a variety of adjustments for sizing the band to individual patient's neck size and/or provides ease of application of the band around the neck of a patient. However, for one reason or another, the patented devices of the prior art fail to provide structure that support the tracheostomy tube in the midline of the stoma, thereby avoiding discomfort and possible injury to the patient due to the tracheostomy tube device being pulled away from the midline position within the trachea from poorly tied cotton tapes or bands containing VELCRO fastening means whose materials, for one reason or another, fail to function in the manner in which they were intended.

U.S. Pat. No. 4,313,437 to Martin, issued Feb. 2, 1982 and U.S. Pat. No. 4,331,144 to Wapner, issued May 25, 1982, both show the use of elastic material foam fabric, and VELCRO fastening means in their designs. The problems in using these materials have been explained previously.

These band type collar devices comprising VELCRO fastening means are designed on a straight line, not allowing for the natural curve of human neck anatomy. When these collars are placed around the neck of a patient, the VELCRO fastening means in the form of tapes tend to slide upwards in the openings of the flanges of the neck plate, causing upward pull on the tracheostomy tube device within the stoma of a patient. This causes pressure to be exerted on the soft tissues of the stoma. Gradual erosion of the soft tissues may occur over a period of time causing the stoma of the tracheostomy to enlarge. The additional weight of ventilator tubing and indwelling suction equipment may contribute to the development of tracheostomy stoma erosion from a constant or an intermittent pulling of the tracheostomy tube device laterally or vertically within the trachea of a patient.

BRIEF DESCRIPTION OF THIS INVENTION

This invention provides novel features for a device for supporting a tracheostomy tube within a stoma surgically opened in the trachea, thus providing tracheal access for airway management in a patient. The device of this invention comprises a front collar piece and a rear collar piece. The front and rear collar pieces are interconnected through a plurality of equally spaced male and female radiopaque plastic snaps that are positioned and placed to interfit one another and to secure the front and rear collar pieces in proper overlapping position extending essentially horizontally around the neck of a patient to supplement the strength of the prior art attachment of the collar pieces to one another.

A neck plate support piece provides support directly over the stoma of a tracheostomy assisting the swivel neck plate of the tracheostomy tube to conform to individual patient's neck anatomies as in the Shiley Disposable Cannula Low Pressure Cuffed Tracheostomy Tube Device, which is well known in the tracheostomy art.

The body of the front and rear collar pieces are curved, rather than designed on a straight line, to better conform to the natural curvature of a patient's neck. The edges of the front and rear pieces of the collar are rounded or squared to help fit the collar to a patient more comfortably. When the collar is properly applied around the neck of a patient, the edges of the front and rear pieces of the collar overlap one another. Another unique feature of this tracheostomy collar is that the tracheostomy tapes extend from the front collar piece to a position of alignment over the rear collar piece. In the preferred embodiment of the present invention, flexible tapes of VELCRO attachment means extend from the interior of the front collar piece. In a second embodiment of the invention the tracheostomy tapes form an integral part of the front collar piece and extend directly from the front neck plate support piece.

The tracheostomy tapes of both the preferred embodiment of the invention and the second embodiment of the invention are also curved to assist in properly aligning and securing both the front and back sides of the collar together around the neck of a patient after they have been properly threaded through the openings in the flanges of the neck plate of the tracheostomy tube device.

A plurality of loops are aligned longitudinally on the outside of the front collar piece. In the preferred embodiment, the loops are also aligned with the flange holes in the neck piece. The tracheostomy tapes are threaded through these loops in order to keep the tracheostomy tapes centered on the outside of the front collar piece. The tracheostomy tapes are then pulled in opposite directions at equal force towards the back of a patient's neck and secured to the rear collar piece.

In a second embodiment of the invention, the tracheostomy tapes extend directly from the neck plate support piece and are threaded directly through the openings in the flanges of the neck plate of the tracheostomy tube device. The neck plate support piece of the tracheostomy collar rests directly on the neck plate of the tracheostomy tube. The tapes are then pulled towards the back of a patient's neck in opposite directions at equal force through loops at the ends of the rear collar piece and secured to the rear collar piece.

The tapes and the front and rear collar pieces are provided with at least a portion of fabric of either rough or soft VELCRO securing means that help provide securement of the collar pieces relative to one another in adjustable overlapping relation to conform the collar length approximately to the neck size of the patient.

When the device is installed properly around the neck of a patient, the tracheostomy tube device is held firmly within the stoma of a tracheostomy within the trachea of a patient. The design of this collar assists in reducing or preventing vertical, horizontal or oblique moments of force that would displace the tracheostomy tube within the stoma, thus potentially avoiding damage to the soft tissues surrounding the stoma, the tracheal wall or underlying vasculature also preventing the inadvertent loss of the airway when the opposite forces previously described deviate from equality sufficiently to displace the neck plate from its initial position of alignment over the stoma.

In addition to the above features, several of the elements of the present device are made of a material having sufficient durability, washability, reusability, breathability, smoothness, low friction and low shear characteristics generally associated with porous polytetrafluoroethylene (PTFE) material, particularly the element exposed directly to the patient.

Porous polytetrafluoroethylene (PTFE) has special features of being durable, washable and reusable. It dries quickly after washing.

A preferred pore size for use in this device is 0.2 microns. However, other types of this membrane fabric may be used in the body of this device.

GORE-TEX ® is a tradename for a superior porous polytetrafluoroethylene (PTFE) material distributed by W. L. Gore Associates, 1505 North 4th Street, Flagstaff, Ariz. 86004.

This PTFE material is a breathable, waterproof material comprising a microporous membrane which permits air and water vapor to pass through but is a barrier to bacteria and water droplets.

The PTFE fabric is breathable, allowing air to cool and dry the patient's skin. It is smooth, it has a low-friction, low-shear quality that helps to prevent skin breakdown.

Porous polytetrafluoroethylene (PTFE) has the capability of being sterilized with either gas or chemical methods currently available in order to be used immediately after surgical insertion of a tracheostomy.

Porous polytetrafluoroethylene (PTFE) is used in medical products such as vascular grafts, in NASA vehicles and in sporting clothing as well as having many other uses.

U.S. Pat. No. 3,953,566 describes a process for producing porous polytetrafluoroethylene (PTFE).

The use of the PTFE material or other material having similar characteristics in facing relation to the stoma of a patient instead of exposure of a cotton tape or VELCRO fastening means to the stoma and its contaminating secretions improves the operation of the device of this invention.

The benefits of this invention will be understood much better in the light of a description of several preferred embodiments thereof, which follows.

BRIEF DESCRIPTION OF THE DRAWINGS

In the drawings that form part of this description of this invention, and wherein like reference numbers are applied to like structural elements.

DESCRIPTION OF PREFERRED EMBODIMENTS

Referring to the drawings, the structural elements of one embodiment of the present invention are shown in FIGS. 1 to 4 as comprising a front collar piece 20 (FIGS. 1, 2, 2A) and a rear collar piece 22 (FIGS. 3, 4, 4A) that cooperate with each other to perform all the functions desired for this invention in a manner to be described. The front collar piece 20 comprises a swivel plate support piece 24 comprising a thin sheet 25 of a firm, flexible plastic foam material having a thickness from one half to the thickness of a swivel plate of a Shiley tube device mentioned earlier. Piece 24 has a central opening 26 flanked by flanges 28 at either longitudinal extremity. Each flange 28 is provided with a transversely extending slotted flange hole 30. Plate support piece 24 corresponds in longitudinal shape to a swivel plate (shown in phantom) pivoted to a tracheostomy tube (shown in phantom). Sheet 25 of plastic support piece 24 is covered on its front major surface by a PTFE covering material 32 that extends into a pair of extension portions 31 and on its rear surface with PTFE covering material 36. A plurality of equally distant, longitudinally aligned loops 34 of PTFE material is provided on the outer surface of each of the extension portions 31 in longitudinal alignment with the flange holes 30. VELCRO fastening means comprising a fabric strip 38 is sewn with stitches 37 over the central portion of the rear PTFE material surface 36 of front collar piece 20 with the soft surface of the strip 38 containing small mating loops exposed. A tape 40 is previously secured by stitches 39 to rear surface 36 to form a layer between the surface 36 and the soft fabric strip 38. Tape 40 has an oblique free end 41 opposite an inner end that is sewn between the exposed fabric strip 38 and the PTFE covering 36. Plastic reinforcement means 42 of radiopaque material is applied to the oblique free ends 41 so as to facilitate threading the tapes 40 through the flange holes 30.

In the embodiment of FIGS. 1 to 4, front collar piece 20 is provided with a plurality of male snaps 43 on rear surface 36 flanking the opposite longitudinally extending sides of VELCRO fastening means included in fabric strip 38.

Figure 3:
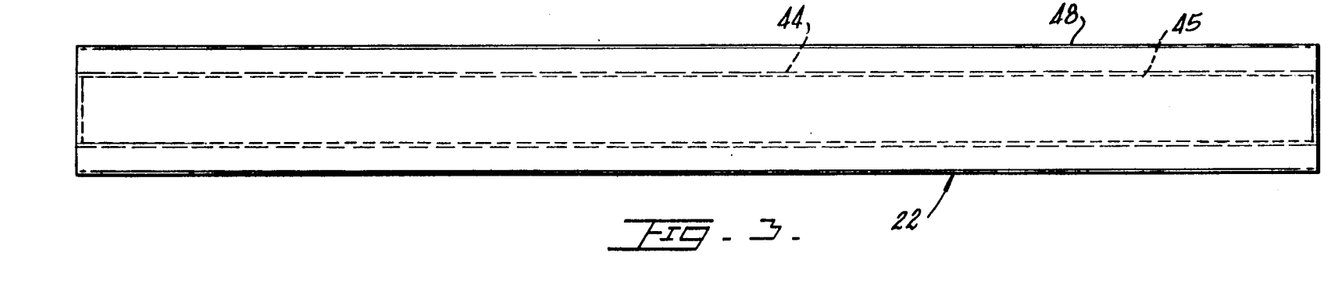
FIG. 3 is a front view of the inside surface of a rear collar piece that cooperates with the front collar piece of FIGS. 1 and 2.
Figure 4:
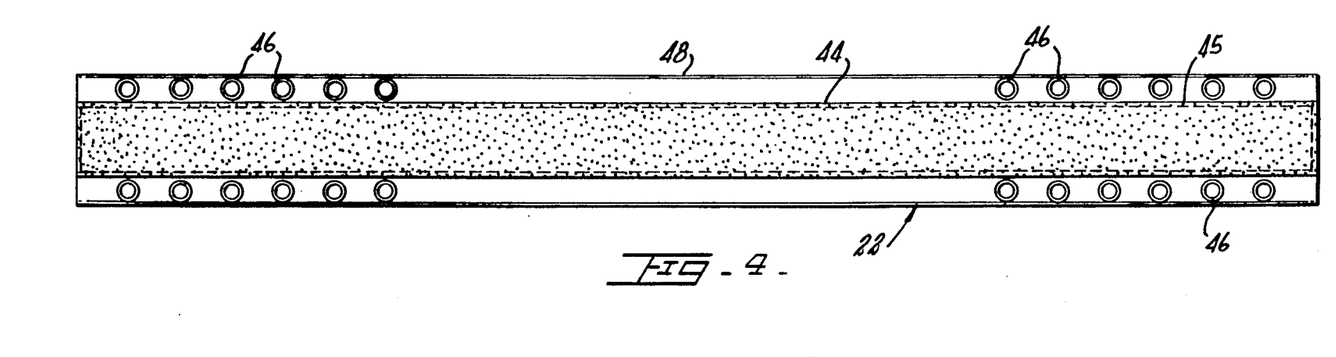
FIG. 4 is a front view of the outside surface of the rear collar piece that engages the inside surface of the front collar piece of FIG. 2.
Figure 4A:
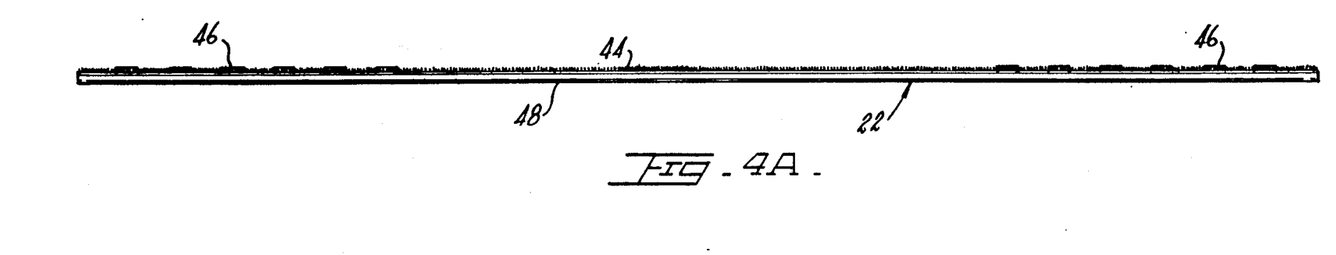
FIG. 4A is a side elevational view of the rear collar piece of FIGS. 3 and 4.
Figure 5:
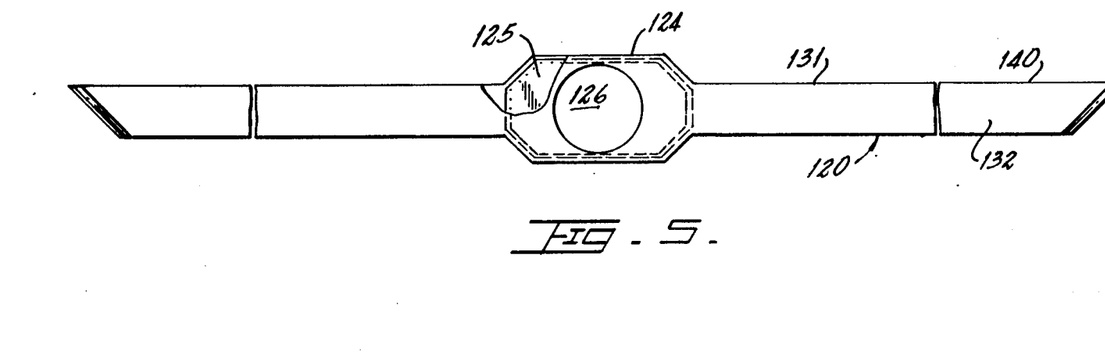
FIG. 5 is a front view of the outside surface of a front collar piece of a second embodiment of the invention that corresponds to the view of FIG. 1.

The rear collar piece 22 depicted in FIGS. 3 and 4 comprises a porous polytetrafluoroethylene (PTFE) material 48 provided with VELCRO fastening means included in a strip 44 sewn with stitches 45 along its length. A rough surface of strip 44 extends with small mating hooks in exposed relation to mate with said small mating loops on said soft surface of fabric strap 38 and has a plurality of female snaps 46 applied to the porous polytetrafluoroethylene (PTFE) material 48 along the edges flanking each longitudinal side of the fabric strip 44 having an exposed rough surface with the PTFE material 48 providing an inner surface for the rear collar piece 22. The female snaps 46 are longitudinally spaced equal distances flanking each side of the strip 44. The female snaps 46 are constructed and arranged for connection with selected ones of a plurality of male snaps 43 applied in longitudinally spaced relation to the front collar piece 20 along its rear surface 36.

Strips 38 and 44 comprise flexible attachment means that interconnect front collar piece 20 to rear collar piece 22 in the same connection regions where male snaps 43 are connected to female snaps 46 when said collar pieces are arranged as a continuous collar around the neck of a patient. It is thus necessary to separate both the flexible attachment means and interfitting snaps in any connection region to open the collar and remove it from the patient's neck.

Figure 9A:
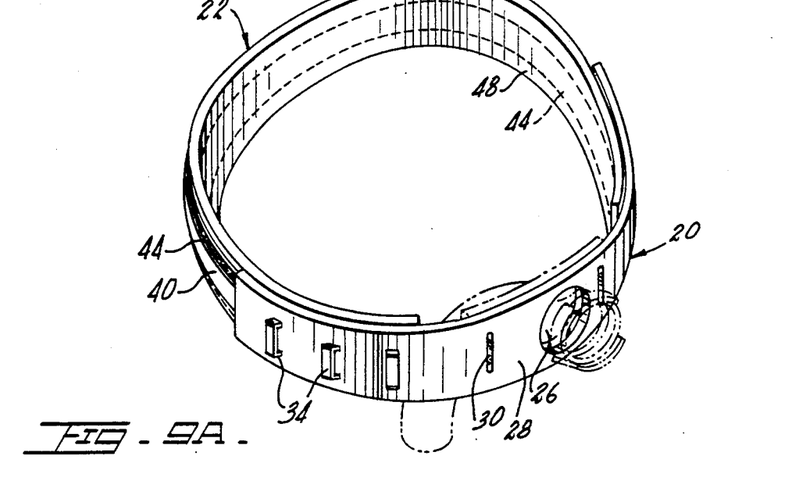
FIG. 9A is a perspective view showing how the collar pieces of the embodiment of FIGS. 1 to 4 are interconnected and used with a Shiley tube device (shown in phantom) according to one embodiment of the assembly.
Figure 9B:
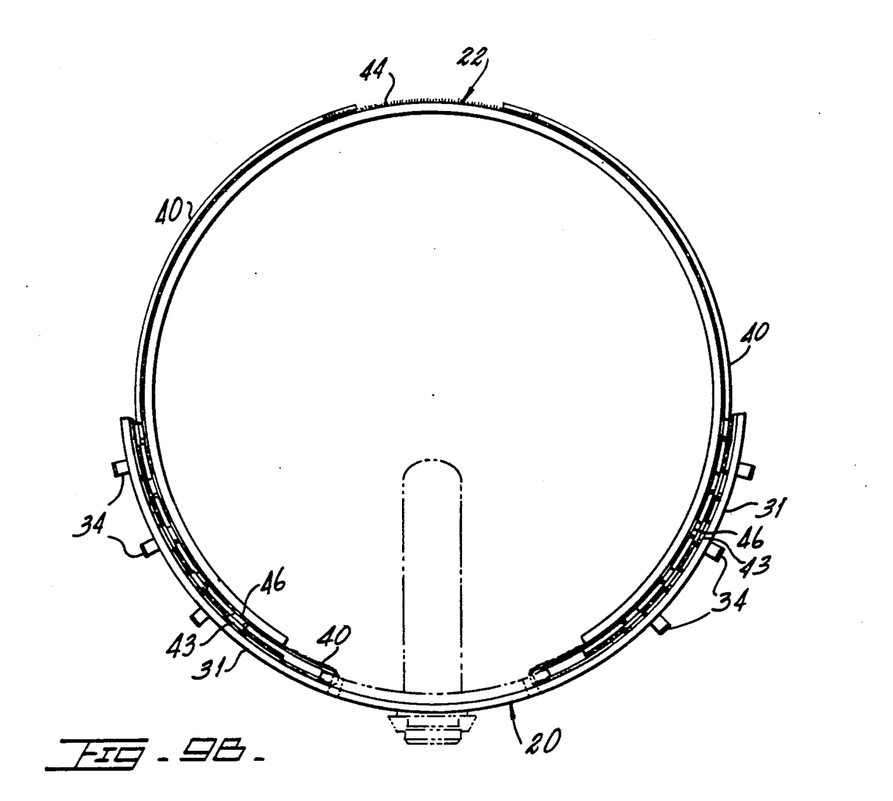
FIG. 9B is a top view of the FIG. 9A assembly.

In order to prepare the device for use, the neck plate support piece 24 is applied to a swivel neck plate of a tracheostomy tube structure such as the Shiley Disposable Cannula Low Pressure Cuffed Tracheostomy Tube Device and the central opening 26 and flange holes 30 of the swivel neck plate support piece 24 are aligned with a corresponding opening and flange holes in the swivel neck plate of the tracheostomy tube structure (shown in phantom in FIGS. 9A and 9B).

The typical dimensions of an approved device according to this invention involves collar pieces having a width of $1\frac{1}{4}''$. The front collar piece 20 has its fabric strip 38 oriented with its soft Velcro surface that faces the patient three-quarters of an inch wide and centered from each end of the front collar piece toward the middle of the shaped and formed tracheostomy plate support piece 24.

Sewn beneath the fabric 38 of VELCRO fastening means and centered on the inner surface 36 of the front collar piece 20 of the tracheostomy collar are the tracheostomy tapes 40 which are two $\frac{3}{8}''$ wide strips 12-14" in length. Tapes 40 are made of the porous polytetrafluoroethylene (PTFE) material with a tape of VELCRO fastening means having its soft surface provided with said small mating loops facing towards the patient. Said tapes extend through flange holes 30 away from the stoma of the patient between inner surface 36 of front collar piece 20 and the patient's neck when properly applied. Therefore, neither tapes 40 nor fabric 38 are directly exposed to the stoma and only inner surface 36 of porous polytetrafluoroethylene material is directly exposed to the contaminating secretions from the stoma.

The tapes 40 are sewn from each end of the two extension portions 31 beneath the fabric 38 of the inner surface 36 of the front collar piece 20. The loose ends 41 of the tapes 40 extend in opposite directions from opening 26 of the neck plate support piece 24 to the opposite side of the front collar piece 20 terminating in reinforcements 42 over their oblique ends 41.

Figures 1, 2:
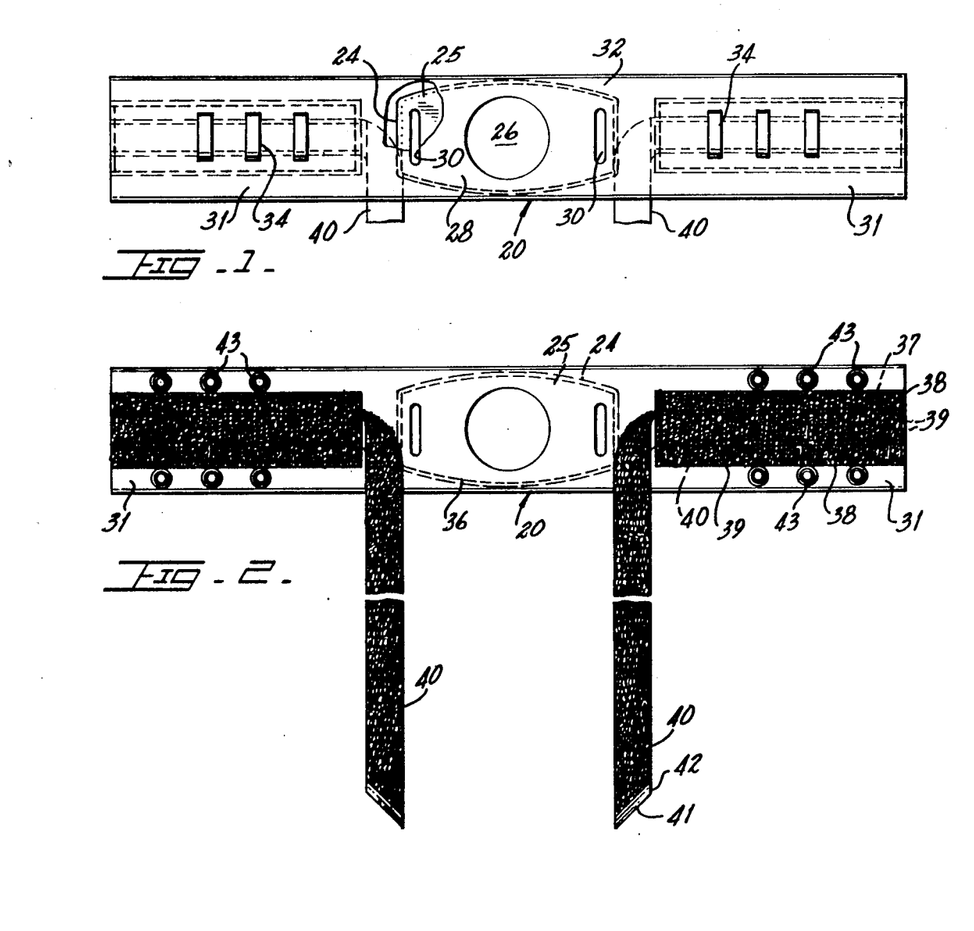
FIG. 1 is a front view of the outer surface of a front collar piece forming part of a preferred embodiment of the present invention.
FIG. 2 is a front view of the inside surface of the front collar piece forming part of said embodiment of the present invention.
Figure 2A:
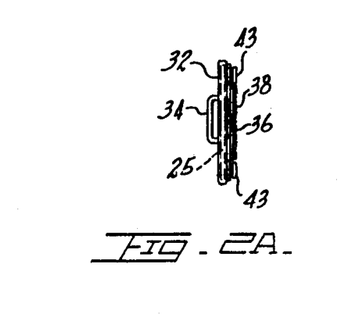
FIG. 2A is an end elevational view of the front collar piece of FIGS. 1 and 2.

The tracheostomy tapes 40 shown hanging loosely in FIG. 2 are designed to be threaded through the openings 30 in the flanges 28 of the neck plate support piece 24 of the front collar piece 20 and extended away from the stoma to avoid exposure of tape to contaminating stoma secretions in one of two methods to be described.

In one method of attaching the front collar piece 20 to the rear collar piece 22, as shown in FIGS. 9A and 9B, the neck plate support piece 24 is applied directly over the neck plate of a tracheostomy tube device (shown in phantom) and laid flat against its surface. The tracheostomy tapes 40 extending from each extension portion 31 of the front collar piece 20 are threaded directly through openings in the flanges of the neck plate then pulled back around and behind the neck of the patient securing the exposed soft surface containing small mating loops of fabric 38 of tracheostomy tapes 40 to the rough exposed surface containing small mating hooks of fabric strip 44 centered along the outside of the rear collar piece 22 (FIG. 4). The closest fitting male snaps 43 and female snaps 46 extending along the longitudinal side edges are snapped together to develop a more permanent attachment.

Figure 10A:
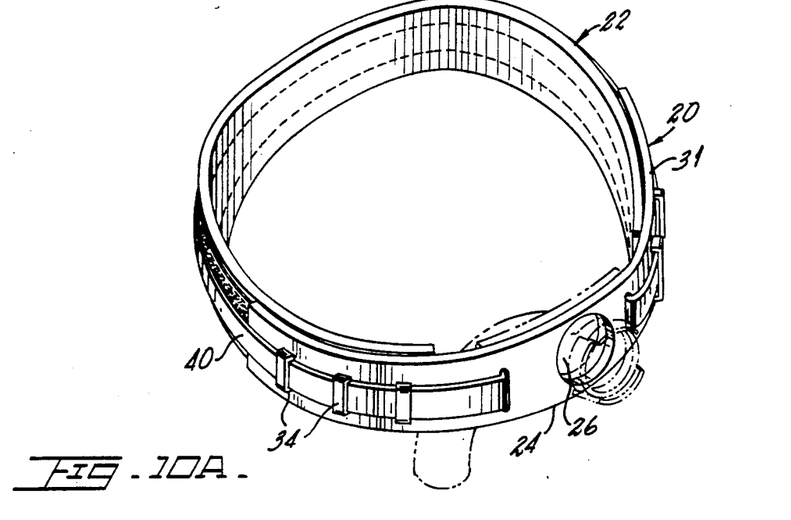
FIG. 10A is a perspective view similar to FIG. 9A showing how the collar pieces are arranged when a second method of interconnection is used to assemble the parts of the FIGS. 1-4 embodiment.
Figure 10B:
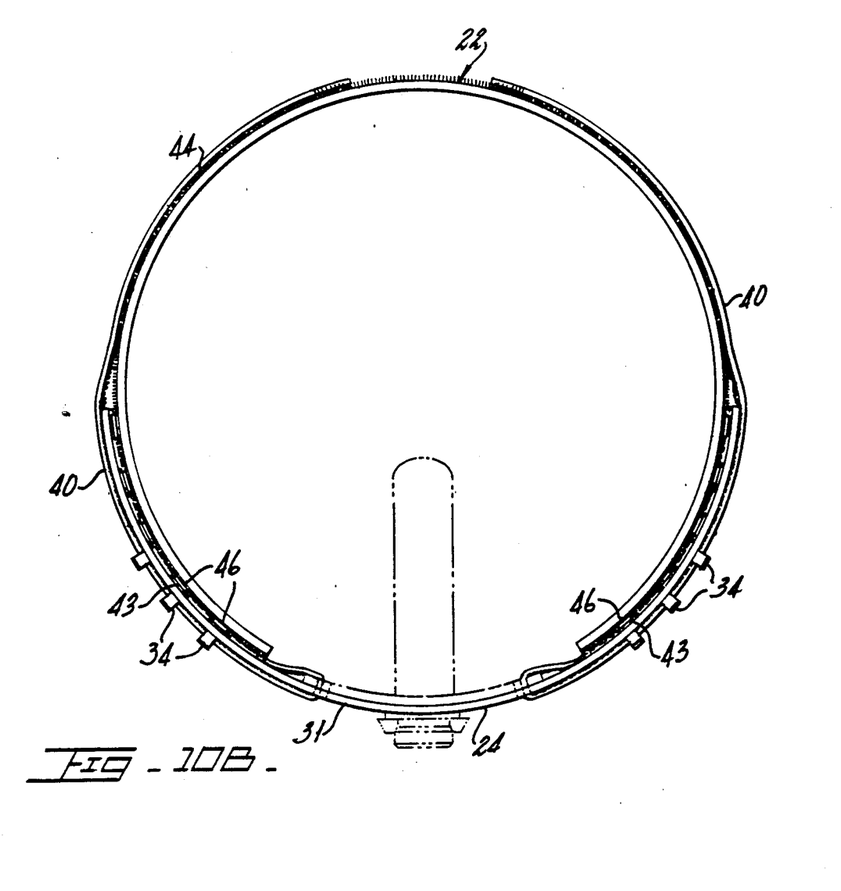
FIG. 10B is a top plan view of the FIG. 10A assembly.

In a second method for assembling the FIGS. 1 to 4 embodiment, depicted in FIGS. 10A and 10B, the neck plate support piece 24 is applied over the tracheostomy tube in the same manner as in the first method. The tracheostomy tapes 40 sewn between porous polytetrafluoroethylene covering 32 and the soft surface of fabric 38 are brought up from behind the neck plate of the tracheostomy tube and threaded through openings in the flanges of the neck plate (shown in phantom) and through the flange holes 30 in the flanges 28 of the neck plate support piece 24 of the front collar piece 20. The tapes are then threaded through the longitudinally aligned PTFE loops 34 to maintain the tracheostomy tapes in the center of the front collar piece 20 as they are drawn back around and behind the neck of the patient, securing the small mating loops of fabric 38 of tracheostomy tapes 40 to the rough exposed surface of fabric strip 44 having small mating hooks to the outside of the rear collar piece 22 (FIG. 4), thus securing the front and rear collar pieces together. Attachment is made permanent by snapping corresponding male snaps 43 to female snaps 46 along the longitudinal flanking lines of front collar piece 20 and rear collar piece 22.

The male snaps 43 and female snaps 46 are preferably made of plastic. Each of the snaps are radiopaque and spaced apart equal distances. The male snaps 43 on the front collar piece 20 are ½" apart and located on two lines flanking the length of the fabric strip containing VELCRO fastening means. A change of one snap spacing for the connections between male snaps 43 and female snaps 46 changes the length of collar 20, 22 comprising overlapping collar pieces by one-half inch and assures that the collar length does not mismatch the neck size by more than one-quarter inch. Three male snaps 43 are provided adjacent each corner of the collar piece containing VELCRO fastening means. Neck plate support piece 24 is formed and shaped to match the exact shape of the Shiley tracheostomy tube swivel neck plate with matching flange holes However, the collar design may be customized to match other brands of tracheostomies The neck plate support piece 24 is sewn into the PTFE material and is manufactured out of a thin, firm flexible foam material which has similar characteristics to the PTFE material. Plastic eyelets, which are also radiopaque, are stamped through the material where the flange holes 30 are located to provide strength and stability, help maintain the shape of the tracheostomy neck plate support piece 24 and allow for easier threading of the tracheostomy tapes 40 through openings 30. The neck plate support piece is sewn into the PTFE material with plastic eyelets stamped through the material where the flange holes are located to provide strength and stability and help maintain the shape of the tracheostomy plate support piece 24.

The PTFE loops 34 are at least three in number although more may be used if desired and the first one is ½" from its adjacent opening 30 of flange 28 on either side with two additional loops evenly spaced at ½" intervals. Both the front neck piece 20 and rear neck piece 22 are ½" thick. The thickness of the body of the collar is provided by a soft, foam material with characteristics similar to that of the PTFE material. This foam material is sewn into the PTFE fabric providing padding for the collar.

The rear collar piece 22 is a solid piece of PTFE material with material comprising VELCRO fastening means having its rough surface provided with said small mating hooks facing away from the patient centered along the back part of the rear collar piece 22. The PTFE material faces the patient. Evenly spaced female snaps 46 are provided on the side of the rear collar piece 22 that faces away from the patient. A total of six snaps are spaced ½" apart from each of the corners of the rear collar piece 22. The spacing between adjacent snaps must be uniform, but need not be one-half inch.

Figure 6:
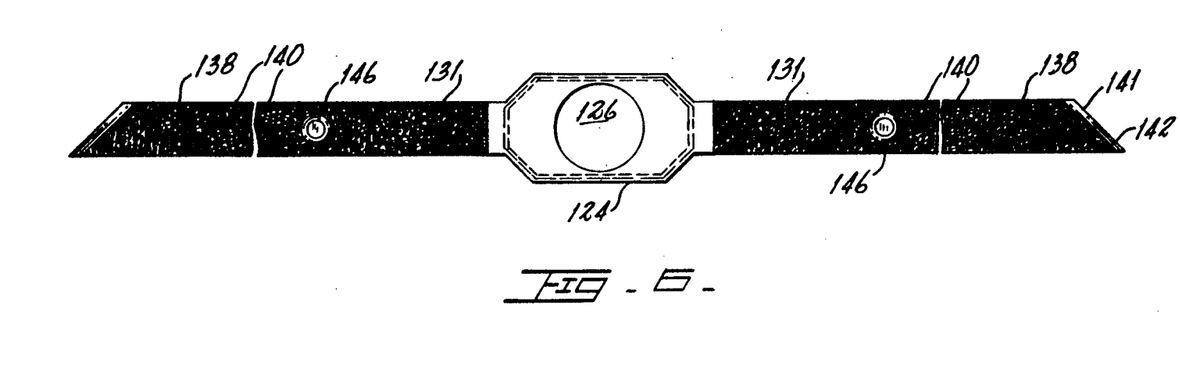
FIG. 6 is a front view of the inside surface of a front collar piece of the second embodiment of the invention that corresponds to the view of FIG. 2.
Figure 6A:
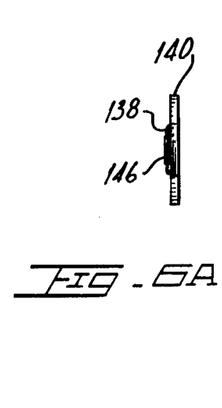
FIG. 6A is an end elevational view of the front collar piece of FIGS. 5 and 6.
Figure 7:
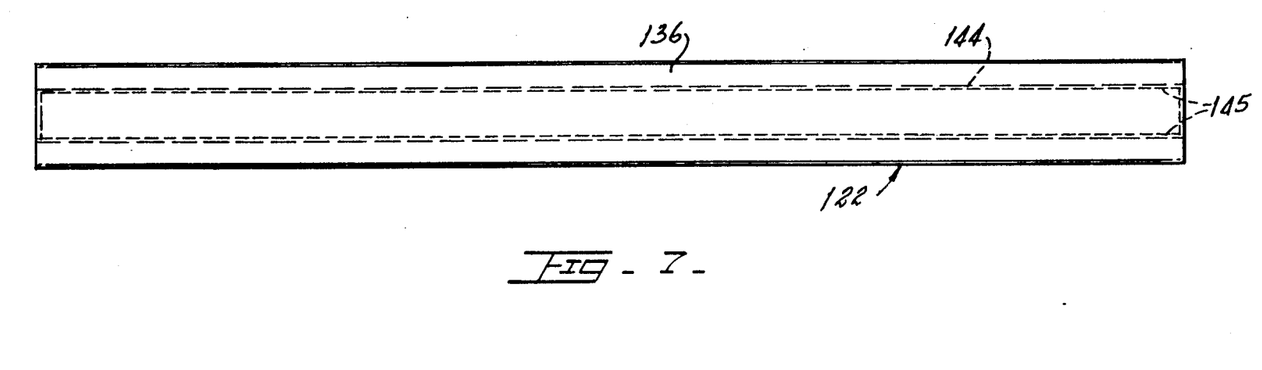
FIG. 7 is a front view of the inside surface of the rear collar piece that cooperates with the front collar piece of FIGS. 5 and 6.
Figure 8:
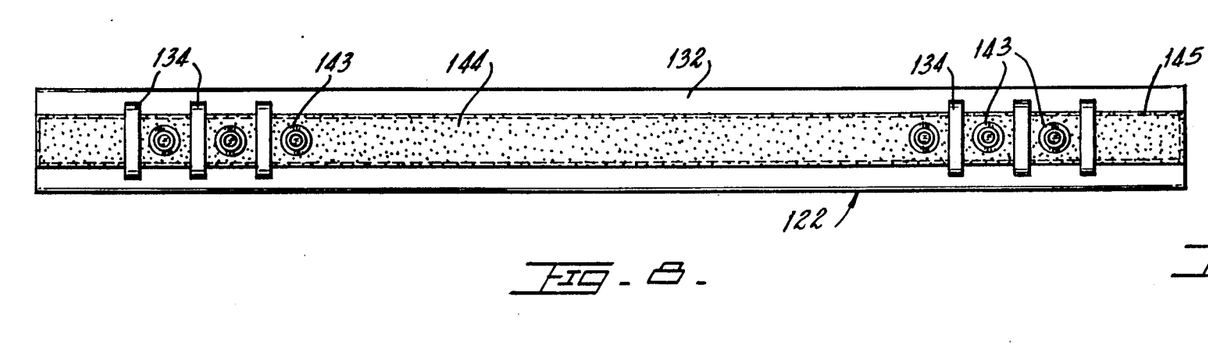
FIG. 8 is a front view of the outside surface of the rear collar piece that cooperates with the inside surface depicted in FIG. 6.
Figure 8A:
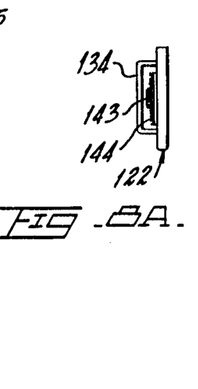
FIG. 8A is an end elevational view of the rear collar piece depicted in FIGS. 7 and 8.

The embodiment of FIGS. 1 to 4 may be modified by eliminating flange holes 30 from front collar piece 120 and providing extensions 131 directly from swivel plate support piece 124 as illustrated in FIGS. 5 to 8, 11A and 11B. The reference numbers applied in FIGS. 5 to 8 are 100 more than those of corresponding elements of the FIGS. 1 to 4 embodiment. For example, the PTFE fabric loops 134 may be attached to the outside surface of the rear collar piece 122 along the ends of a fabric strip 144 comprising VELCRO fastening means that extends the entire length of its porous polytetrafluoroethylene material 132 with male snaps 143 spaced at equal distances in two sets in one row along the transverse center near each longitudinal end thereof as shown in FIG. 8 to mate with female snaps 146 extending through the center line of front collar piece 120 near the ends thereof as shown in FIG. 6.

Figure 11A:
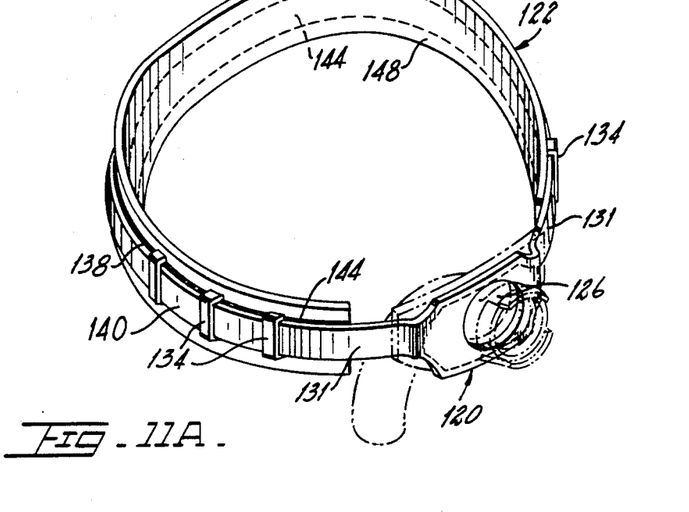
FIG. 11A is a perspective view similar to FIGS. 9A and 10A, showing how the elements of the embodiment of FIGS. 5 to 8 are interconnected.
Figure 11B:
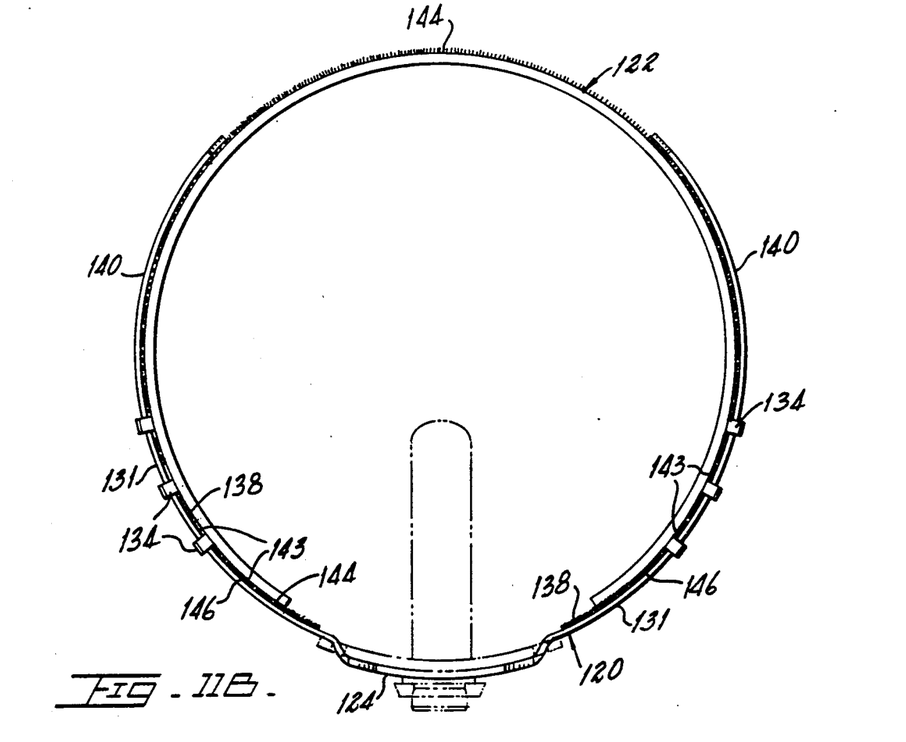
FIG. 11B is a top plan view of the FIG. 11A assembly.

The embodiment of FIGS. 5 to 8 is assembled by aligning neck plate support piece 24 over the tracheostomy tube and pulling both extensions 131 that extend into tapes 140 around the patient's neck and threading tapes 140 through PTFE loops 134 at the ends of the rear collar piece 122 held against the back of the neck of a patient. After checking for proper alignment, the soft surface of fabric strip 138 containing VELCRO fastening means on each end of extensions 131 or tape 140 is attached to rough surface of fabric strip 144 containing VELCRO fastening means along the central area of rear collar piece 122. Attachment is made more permanent by snapping the closest fitting snaps 143 on rear collar piece 122 to snaps 146 on front collar piece 120. This latter assembly is shown in FIGS. 11A and 11B.

The circular shape of central opening 26 depicted in the drawings may be replaced with openings of other outline shapes such as rectangular or polygonal, for example. Also, the female snaps 46 or 146 may be applied to the rear collar piece 22 or 122 and male snaps 43 or 143 may be applied to front collar piece 20 or 120 while the rough surface of fabric strip 44 or 144 with small mating hooks may be applied to the inside surface of the front collar piece 20 or 120 and the soft surface of fabric strip 38 or 138 containing VELCRO fastening means with small mating loops may be applied to the outside surface of the rear collar piece 22 or 122 as alternate embodiments.

The application of the neck plate support piece 24 or 124 directly over the stoma followed by pulling tapes 40 or 140 extending from front collar piece 20 or 120 in opposite directions with equal force maintains the tracheostomy tube device in proper alignment with the stoma. In contrast, prior art devices that extend tapes from the rear collar piece do not contribute to maintaining this alignment. In addition, the present invention provides, to supplement the tie knotting procedure and the fastener containing VELCRO fastening means of the prior art, cooperating snaps that retain the two pieces of the collar attached together even after the other means of attachment of the prior art fail, and loop means for extending the two tapes 40 in a straight line in opposite directions to cause equal and opposite forces in a horizontal direction when applied to the neck of a patient so as to avoid moving the tracheostomy tube relative to the midline position within the stoma. Therefore this invention reduces the risk of inadvertent loss of the airway due to fabric containing VELCRO fastening means becoming loose due to normal wear and tear resulting from repeated washings and regular use. There is no need to replace the device every eight to twelve hours as is the case with tracheostomy tapes loosening or having badly soiled collars of material having VELCRO fastening means that require frequent replacement, which the porous polytetrafluoroethylene (PTFE) material of this invention avoids. The present invention reduces trauma to the skin of the neck of a patient because of its softer wider base of support than that of the prior art, particularly in tracheostomy ties that can cause skin breakdown in patients when tightly tied or soiled. The PTFE material has such characteristics that the device may be left on a patient during regular bathing and during care of the tracheostomy stoma as the PTFE material may be washed with soap and water and dried with a towel or blow dried while on a patient. The present structure provides easy access to a tracheostomy stoma for routine cleaning or a dressing change for the tracheostomy. The present invention may be worn easily and comfortably beneath a cervical collar. The PTFE material is breathable, it does not stain, it resists odor, it is durable, washable and reusable and may be sterilized with chemical or with gas for use in immediate post operative tracheostomy patients without compromising asepsis. The neck plate support piece of this invention provides support over the tracheostomy plate and reduces vertical and horizontal pull as well as oblique pull of the tube against the walls of the tracheostomy stoma which happens frequently with traditional tracheostomy ties and with loosening attachments containing VELCRO fastening means when heavy ventilator tubing lies to one side of the patient to cause uneven pull, the addition of an indwelling suction apparatus adds its weight to the ventilator tubing, or ventilator tubing pulling on the tracheostomy stoma during the rotation of a rotatable bed.

According to the provisions of the patent statutes, the principle of this invention has been explained and what is now considered to represent its best embodiment and some variations have been illustrated and described. However, it is understood that, within the scope of the claimed subject matter that follows, the invention may be practiced otherwise than as specifically illustrated and described.

What is claimed is:

1. A device for supporting and maintaining a tracheostomy tube in a midline position relative to the stoma of a tracheostomy, said tracheostomy tube being supported for limited movement so that it does not apply pressure against the walls of said stoma sufficient to harm a patient, said device comprising a front collar piece having a pair of ends and a central portion constructed and arranged to support said tracheostomy tue in said midline position, and a rear collar piece, the total length of said front collar piece and said rear collar piece being longer than the circumference of a neck of said patient, an extension portion extending longitudinally from each end of said front collar piece to provide a pair of overlapping portions, each of the latter overlapping an end portion of said rear collar piece to form an attachment region, each of said overlapping portions and end portions having an exposed surface portion containing flexible fastening means located in one or the other of said attachment regions remote from said stoma, said flexible fastening means comprising small mating loops or small mating hooks on said overlapping portions and said end portions, said small mating hooks and said small mating loops being constructed and arranged to secure one of said overlapping portions to one of said end portions in one of said attachment regions and the other of said overlapping portions to the other of said end portions in the other of said attachment regions, a first set of longitudinally spaced snaps supported on each of said extension portions, a second set of cooperating, longitudinally spaced snaps supported on each of said end portions and constructed and arranged for securement to said first set of snaps, said sets of snaps being applied to said overlapping portions and said end portions in said attachment regions also occupied by said flexible fastening means, said snaps and said flexible fastening means being constructed and arranged to convert said device into a continuous collar of adjustable length surrounding the neck of said patient when properly interconnected, said continuous collar thereby being constructed and arranged to be separated from said neck only by completely disconnecting both said flexible attachment means and said snaps in said either one of said attachment regions.

2. A device as in claim 1, wherein one of said collar pieces is provided with a first series of aligned, longitudinally spaced loops for receiving one of said extension or end portions and a second series of aligned, longitudinally spaced loops for receiving the other of said extension or end portions.

3. A device as in claim 2, wherein said series of loops are provided along said front collar piece.

4. A device as in claim 2, wherein said series of loops are provided along said rear collar piece.

5. A device as in claim 2, wherein said flexible fastening means are supported on flexible tapes having obliquely extending ends.

6. A device as in claim 5, further including plastic reinforcements of radiopaque material applied to said obliquely extending ends.

7. A device as in claim 1, wherein said snaps of each of said sets are longitudinally spaced one-half inch apart to make possible a maximum difference between adjusted collar length and neck size of no more than one-quarter inch.

8. A device as in claim 1, wherein said snaps are supported along opposite longitudinal edges of said front collar piece and said rear collar piece along the length of said attachment regions occupied by said flexible fastening means.

9. A device as in claim 1, wherein said snaps are supported along the longitudinal center portion of said front collar piece and said rear collar piece along the length of said attachment regions occupied by said flexible fastening means.

10. A device as in claim 1, wherein the surface of said front collar portion in closest adjacency to said stoma is composed of a waterproof material having sufficient durability, washability, reusability, breathability, smoothness, low friction and low shear characteristics generally associated with porous polytetrafluoroethylene.

* * * * *